(12) United States Patent
Li (10) Patent No.: US 11,019,946 B2
(45) Date of Patent: Jun. 1, 2021

(54) HEAD AND NECK REST DEVICE

(71) Applicant: Jia-Huei Li, Tainan (TW)

(72) Inventor: Jia-Huei Li, Tainan (TW)

( * ) Notice: Subject to any disclaimer, the term of this patent is extended or adjusted under 35 U.S.C. 154(b) by 0 days.

(21) Appl. No.: 16/727,061

(22) Filed: Dec. 26, 2019

(65) Prior Publication Data

US 2020/0205591 A1 Jul. 2, 2020

(30) Foreign Application Priority Data

Dec. 28, 2018 (TW) ................................ 107147716

(51) Int. Cl.
*A47G 9/10* (2006.01)

(52) U.S. Cl.
CPC .............. *A47G 9/1081* (2013.01); *A47G 9/10* (2013.01); *A47G 9/109* (2013.01); *A47G 9/1054* (2013.01); *A47G 9/1072* (2013.01)

(58) Field of Classification Search
CPC ...... A47G 9/10; A47G 9/1054; A47G 9/1072; A47G 9/1081; A47G 9/109; A47G 2009/1018
See application file for complete search history.

(56) References Cited

U.S. PATENT DOCUMENTS

| | | | | |
|---|---|---|---|---|
| 2,765,480 A * | 10/1956 | Mueller | .................. | A47C 7/383 5/640 |
| 2,952,856 A * | 9/1960 | Ruff | ......................... | A47G 9/10 5/640 |
| 3,672,364 A * | 6/1972 | Rankin | ..................... | A61G 7/05 5/621 |
| 3,897,777 A * | 8/1975 | Morrison | .................. | A61F 5/34 5/622 |
| 4,031,578 A * | 6/1977 | Sweeney | ................ | A47C 7/383 5/426 |
| 4,506,396 A * | 3/1985 | Ritchie, Jr. | ........... | A47C 20/023 5/631 |

(Continued)

FOREIGN PATENT DOCUMENTS

| | | |
|---|---|---|
| CN | 2049883 U | 12/1989 |
| TW | M432366 M | 7/2012 |

(Continued)

OTHER PUBLICATIONS

Travel pillow, VeryBuy, "https://www.verybuy.cc/user_submit/item/1727975", originally published Feb. 5, 2018.

*Primary Examiner* — Robert G Santos
*Assistant Examiner* — Rahib T Zaman
(74) *Attorney, Agent, or Firm* — Rosenberg, Klein & Lee (57) ABSTRACT

A head and neck rest device includes two pillow bodies and two head support blocks. The two pillow bodies each have a first end portion and a second end portion. A neck support strap is connected between two opposing sides of the two pillow bodies. The two head support blocks are coupled to the first end portions of the two pillow bodies. The two head support blocks gradually extend downward from the two opposing sides, respectively. The two pillow bodies and the two head support blocks can fully surround the user's head, and do not abut against the two sides of the user's cheek, so as to avoid the occurrence of temporomandibular arthritis. The head and neck rest device can achieve the purpose of relaxation and rest.

9 Claims, 11 Drawing Sheets

(56) References Cited

U.S. PATENT DOCUMENTS

| | | | | | |
|---|---|---|---|---|---|
| 4,528,981 | A | * | 7/1985 | Behar | A61F 5/055 |
| | | | | | 5/637 |
| 5,044,026 | A | * | 9/1991 | Matthews | A47G 9/1054 |
| | | | | | 5/644 |
| 5,265,625 | A | * | 11/1993 | Bodman | A61F 5/3707 |
| | | | | | 128/870 |
| 5,305,754 | A | * | 4/1994 | Honeywell | A61F 5/05883 |
| | | | | | 128/870 |
| 5,505,523 | A | * | 4/1996 | Wang | A47C 7/383 |
| | | | | | 128/870 |
| 5,657,766 | A | * | 8/1997 | Durham | A61F 5/05883 |
| | | | | | 5/637 |
| 5,864,904 | A | * | 2/1999 | Rudick | A47G 9/10 |
| | | | | | 5/490 |
| 6,560,800 | B1 | * | 5/2003 | Draves | A47C 20/023 |
| | | | | | 5/630 |
| 6,581,227 | B1 | * | 6/2003 | Obermaier | A47C 7/14 |
| | | | | | 5/654 |
| 6,641,220 | B2 | * | 11/2003 | Clegg | A47C 7/383 |
| | | | | | 297/397 |
| 2015/0245967 | A1 | * | 9/2015 | Horng | A47G 9/1081 |
| | | | | | 128/845 |
| 2018/0368593 | A1 | * | 12/2018 | Bourgeois | A47G 9/1009 |
| 2019/0167020 | A1 | * | 6/2019 | Bice | A47C 7/383 |

FOREIGN PATENT DOCUMENTS

| | | |
|---|---|---|
| TW | I422344 B | 1/2014 |
| TW | M551891 U | 11/2017 |

\* cited by examiner

HEAD AND NECK REST DEVICE

FIELD OF THE INVENTION

The present invention relates to a neck pillow structure that does not abut against two sides of a user's cheek when in use, so as to avoid the occurrence of temporomandibular arthritis.

BACKGROUND OF THE INVENTION

When people work, use computers, watch TV or take public transportation, they need to maintain a certain posture for a long time. The muscles of the neck and shoulder are tensed to cause muscle pains and soreness. In severe cases, it will hinder the circulation of blood in the brain and oxygen supply, and a person cannot concentrate his/her attention. Therefore, it is necessary to use a neck pillow when sitting. The neck pillow generally has a U shape, and is placed on the user's neck to support the neck.

A common neck pillow structure, as disclosed in Taiwan Utility Model Publication No. M551891 titled "retractable neck pillow" published on Nov. 21, 2017, comprises a U-shaped support pillow body. The support pillow body can be restored to its original shape after compression, and is characterized in that an annular fastening sleeve is sewn on the back of the support pillow body, facing away from the opening. The free end of the annular fastening sleeve is formed with a loop, and a rope capable of retracting the opening of the loop is insertedly disposed in the loop. The opening of the annular fastening sleeve on the back of the support pillow body can be reversely extended toward the opening of the support pillow body, so that the entire support pillow body can be covered in the annular fastening sleeve. Then, the rope in the loop is tightened, which can effectively reduce the volume of the entire support pillow body for storage and carrying. It is convenient for the user to carry and store the neck pillow.

The U-shaped support pillow body of the above-mentioned patent surrounds the neck and cheek of the user, so atlanto-occipital joints and the temporomandibular joints of the cheek are pressed by improper pressure, and it is easy to cause temporomandibular arthritis. The temporomandibular joint is different from other joints in the body. It is a special, slidable joint that connects the skull and mandible. The upper end of the temporomandibular joint is a recessed glenoid fossa of the temporal bone, the lower end of the temporomandibular joint is a condyle of the mandible, and the middle of the temporomandibular joint is connected with the meniscus. Temporomandibular joint abnormalities, also known as temporomandibular joint syndrome, muscle facial pain syndrome, referred to as temporomandibular arthritis, including hearing impairment, ear pain, ear occlusion, tinnitus, the temporomandibular joint has a clicking noise when opening the mouth, the mouth cannot be opened when having a headache, burning pain of the temple, cheek and paranasal sinuses, neck pain, and so on. Therefore, a proper pillow can avoid the occurrence of temporomandibular arthritis (Data Source: Dr. Ke Zhengyu-temporomandibular arthritis).

(https://www.ntuh.gov.tw/ENT/DocLib11/%E6%9F%AF%E6%94%BF%E9%83%81.aspx).

Taiwan Utility Model Publication No. M432366 discloses a "balance pillow" published on Jul. 1, 2012. The head and neck of the human body are very fine and important parts. Most diseases come from the head and neck, and most of which are caused by incorrect postures. Among them, the adverse effect of sleeping posture is the biggest. The diseases caused by the neck directly affect the flow of blood and nerves. As a result, the function of the head cannot be perfected. Over time, the blood supply is insufficient, the brain is dulled, aging, and diseased, making the action inadequate and affecting the physical and mental health. The balance pillow of the above-mentioned patent includes a main body. The main body has a wavy upper surface. The upper surface is divided into a first raised portion and a second raised portion which extend transversely. A concave portion is formed between the first raised portion and the second raised portion. The first raised portion is higher than the second raised portion. A first recess is disposed between the first raised portion and the concave portion. A second recess is disposed between the second raised portion and the concave portion. The interior of the first and second recesses is arc-shaped. The maximum diameter of the opening of the first or second recess is less than the smallest diameter of the occipital bone of the skull of an adult, child or infant, so that the occipital bone can abut against the first recess or the second recess, thereby providing a balanced bearing effect for the occipital bone. The occipital bone can evenly contact the first recess or the second recess without any displacement.

The occipital bone is located at the back of the human head, and the occipital bone is located at the back of the skull. The lower part of the occipital bone has a large oval opening, called the foramen magnum, through which the medulla oblongata passes, linking the spinal cord and brain. Both sides of the posterior edge of the foramen magnum are the neck ligament and the occipital muscles. The superior nuchal line is where the trapezius and sternocleidomastoid muscle are attached. The inferior nuchal line is where both RCPmin and RCPmaj muscles are attached. The occipital bone is symmetric to the sacrum of the spine and corresponds to various organs of the human body. When the occipital bone is displaced due to compression, the corresponding sacrum and the corresponding organs of the human body will have problems. As a result, the body often suffers from back pain, discomfort or illness. Therefore, a so-called "head's sacrum balance therapy" has been developed, especially related to the nervous system, musculoskeletal system, vascular system, lymphatic system, endocrine system and respiratory system. Once the occipital bone and the sacrum are compressed and cause abnormalities, it will inevitably cause major damage to the above-mentioned various human systems. Therefore, the occipital bone plays a very important role in human health.

The balance pillow of the above-mentioned patent can effectively provide a balanced bearing effect for the occipital bone, and the occipital bone can be balanced and not displaced, thereby ensuring the health of the user. But, the balance pillow can only be used when the user lies down, and it cannot be used to rest the neck when the user sits up, and it does not solve the problem that the temporomandibular joints on both cheeks are injured by compression.

Taiwan Patent Publication No. 1422344 discloses a "cushion structure" published on Jan. 11, 2014. The cushion structure includes at least two cushions. Two ends of the least two cushions are connected with connecting belts, respectively. The other end of each connecting belt is connected with an adjusting belt. The end of the adjusting belt is provided with a fixing part. Through the fixing part, the adjusting belt can form a closed loop. By adjusting the length of the adjusting belt, the cushion is retained at a desired position as a support for the user's head, back, waist or neck, so as to achieve a comfortable sitting and lying.

Figure 11:
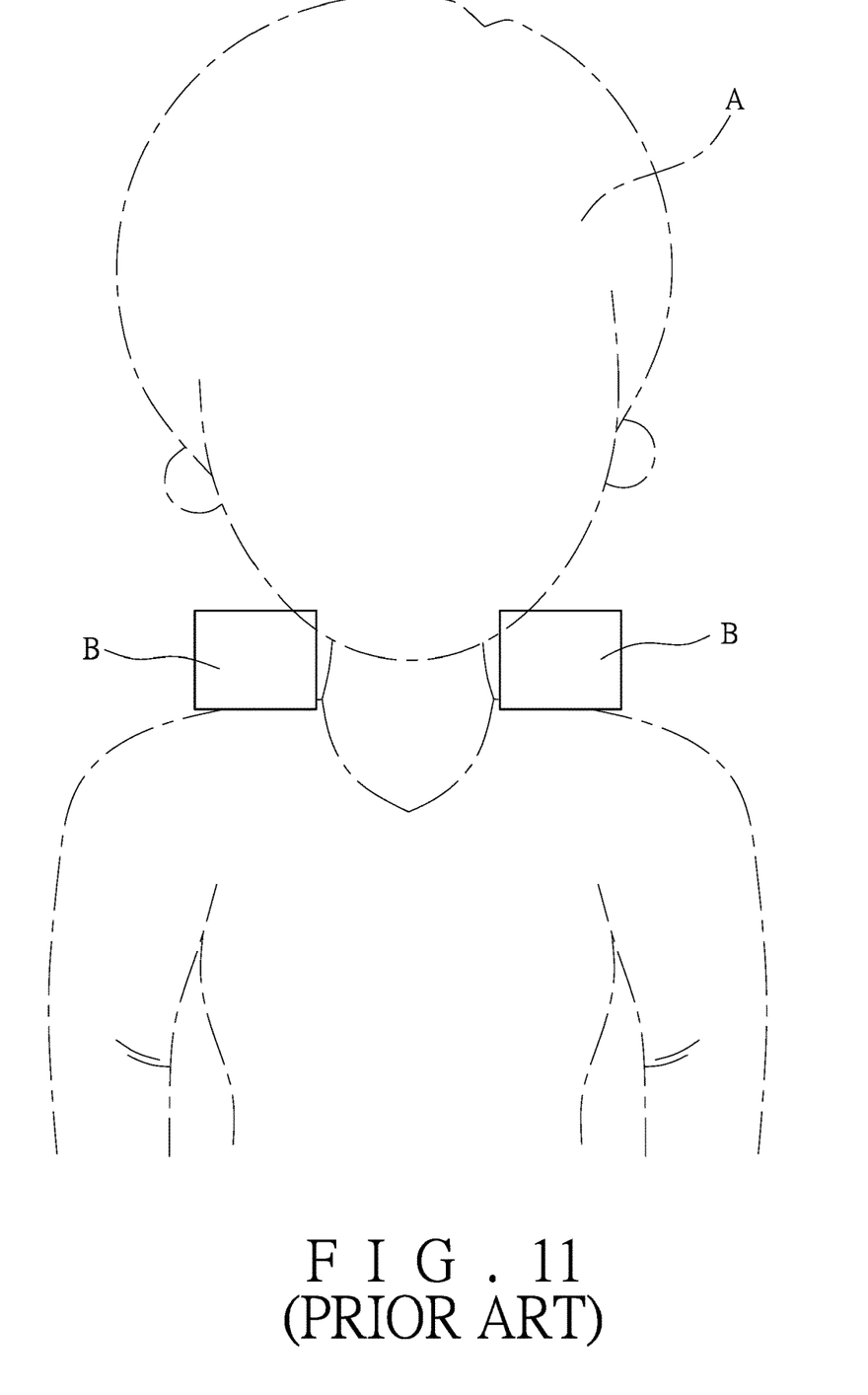
FIG. 11 is a schematic view showing that the user's head and neck rest on a conventional travel pillow.

However, when in use, the user's head (A) and neck lean against the two elongate cushions (B) (as shown in FIG. 11 of the above-mentioned patent). The head (A) and the two cushions (B) are perpendicular to each other at 90 degrees. The cushion (B) doesn't correspond to the outlines of the neck and the head and doesn't support the neck, so it is still not ideal in use.

SUMMARY OF THE INVENTION

The primary object of the present invention is to solve the above-mentioned problems and to provide a head and neck rest device, comprising two pillow bodies and two head support blocks. The two pillow bodies each have a first end portion and a second end portion. A neck support strap is connected between two opposing sides of the two pillow bodies. The two head support blocks are coupled to the first end portions of the two pillow bodies. The two head support blocks gradually extend downward from the two opposing sides, respectively.

Preferably, the two pillow bodies are filled with an elastic filler selected from one of foam, air, cotton and silicone.

Preferably, the two pillow bodies are elongate arc-shaped blocks or elongate straight blocks.

Preferably, the two head support blocks are arc-shaped concave blocks.

Preferably, the two head support blocks are integrally formed with the two pillow bodies.

Preferably, the two head support blocks are filled with an elastic filler selected from one of foam, air, cotton and silicone.

Preferably, the head and neck rest device further comprises a non-slip layer. The non-slip layer is connected between the first end portions of the two pillow bodies and between the two head support blocks. The non-slip layer is made of a material with a high non-slip coefficient.

Preferably, a fastener is connected between the second end portions of the two pillow bodies. The fastener includes a male fastening member and a female fastening member, so that the male fastening member and the female fastening member are fastened to each other.

The above technical features preferably have the following advantages:

1. The two first end portions of the two pillow bodies and the two head support blocks correspond to the outline of the user's head. The neck support strap can generate a supporting balanced force on the user's neck for supporting the center of gravity of the head, so that the head and the neck are kept in a straight line without being offset arbitrarily.

2. The first end portions of the two pillow bodies and the two head support blocks can surround the head completely, and do not abut against the two sides of the user's cheek. Thus, the head will not skew or lean forward due to muscle relaxation, or the muscles of the neck, the spine and the temporomandibular joint will not be injured by compression, stretching and malocclusion. Therefore, the present invention can achieve the purpose of relaxation and rest.

3. Through a gap formed between the neck support strap and the seat back, air can be circulated and ventilated to dissipate heat, so as to prevent the two pillow bodies from being stuffy when the user's head is rested on the pillow bodies.

4. Through the two first end portions, the two head support blocks and the neck support strap, the head and the neck can be suspended to form a large-area space, which is beneficial to ventilate and dissipate heat, so as to achieve a comfortable and cool effect.

5. The non-slip layer made of a material with a high non-slip coefficient can generate a large frictional force, thereby preventing the two pillow bodies from sliding relative to the seat back. It can be more comfortable and stable during sleep.

6. The overall structure of the two pillow bodies combined with the neck support strap and the two head support blocks can support the user's head and neck effectively and stably, without touching the two sides of the user's cheek, so it can effectively prevent the temporomandibular arthritis, so as to ensure the user's health.

DETAILED DESCRIPTION OF THE PREFERRED EMBODIMENTS

Embodiments of the present invention will now be described, by way of example only, with reference to the accompanying drawings.

Figure 1:
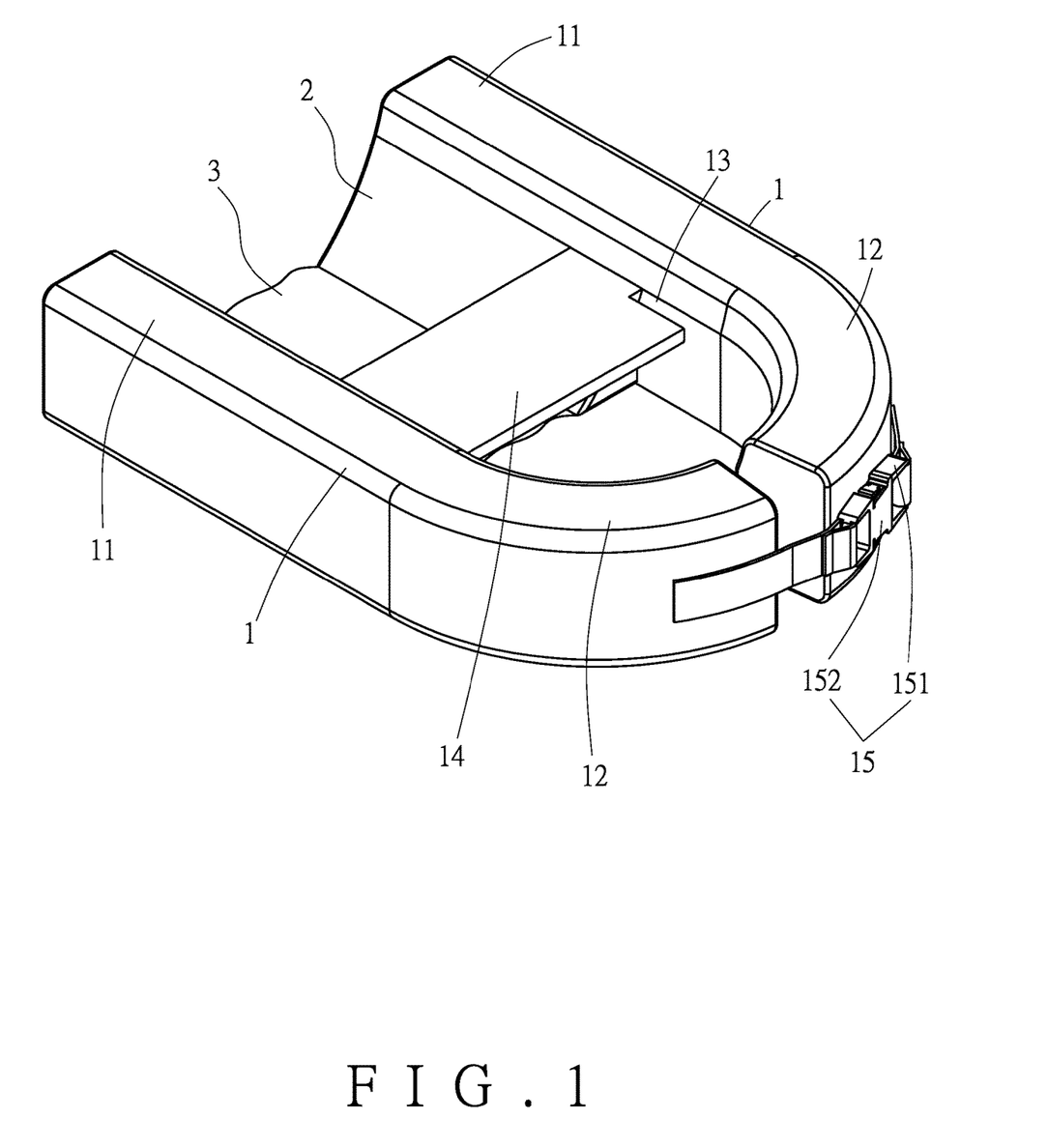
FIG. 1 is a perspective view in accordance with a first embodiment of the present invention.
Figure 2:
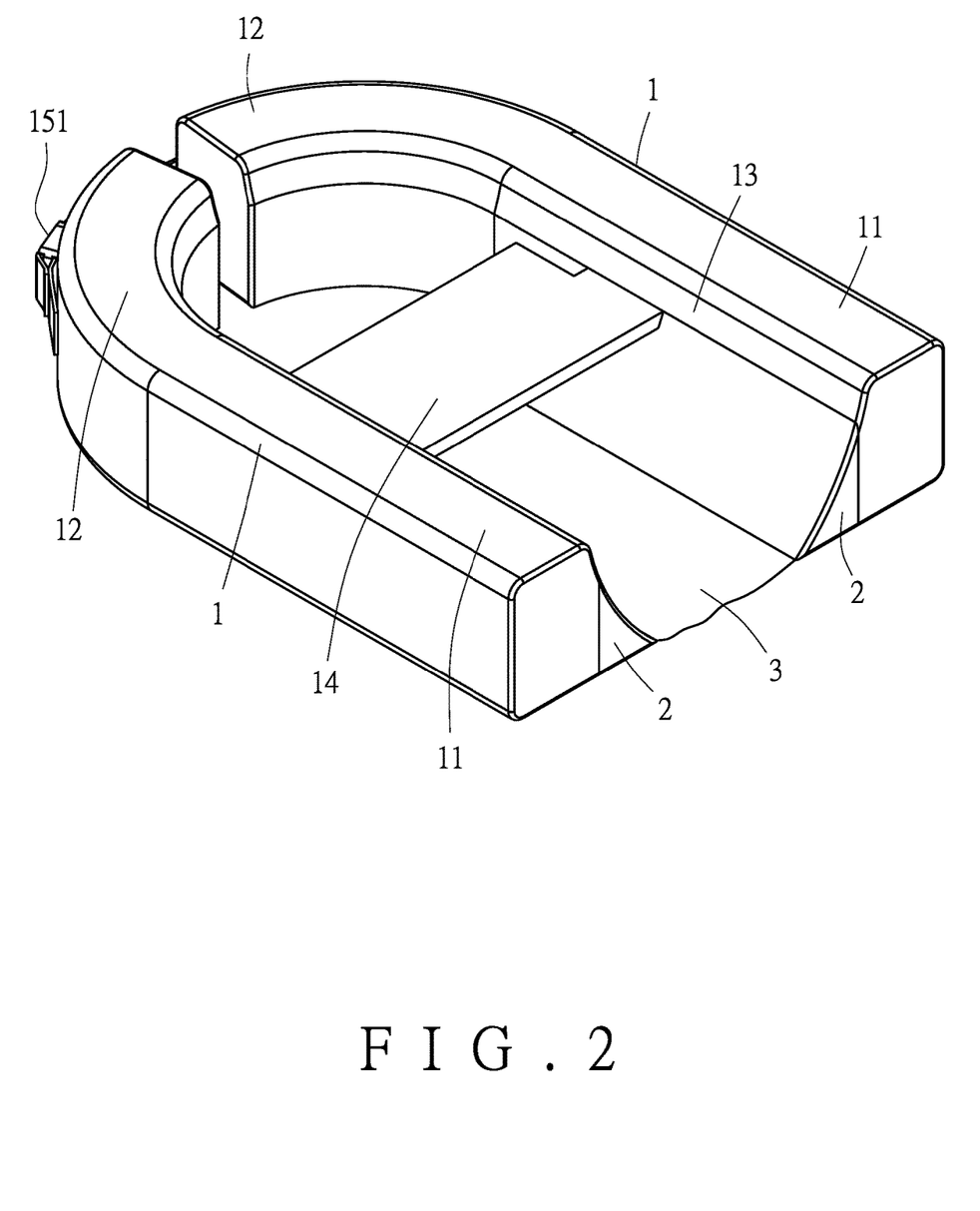
FIG. 2 is another perspective view in accordance with the first embodiment of the present invention.

As shown in FIG. 1 and FIG. 2, a head and neck rest device according to an embodiment of the present invention comprises two pillow bodies (1), two head support blocks (2), and a non-slip layer (3).

Figure 3:
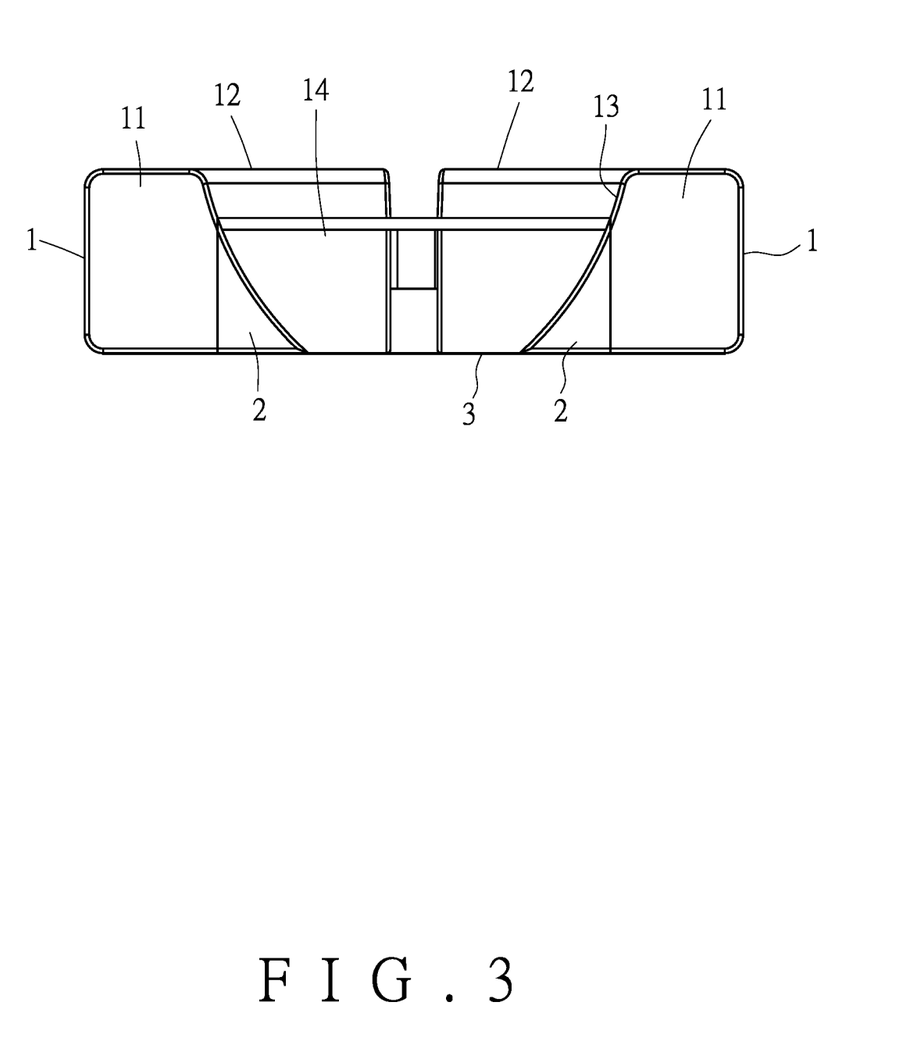
FIG. 3 is a front view in accordance with the first embodiment of the present invention.
Figure 4:
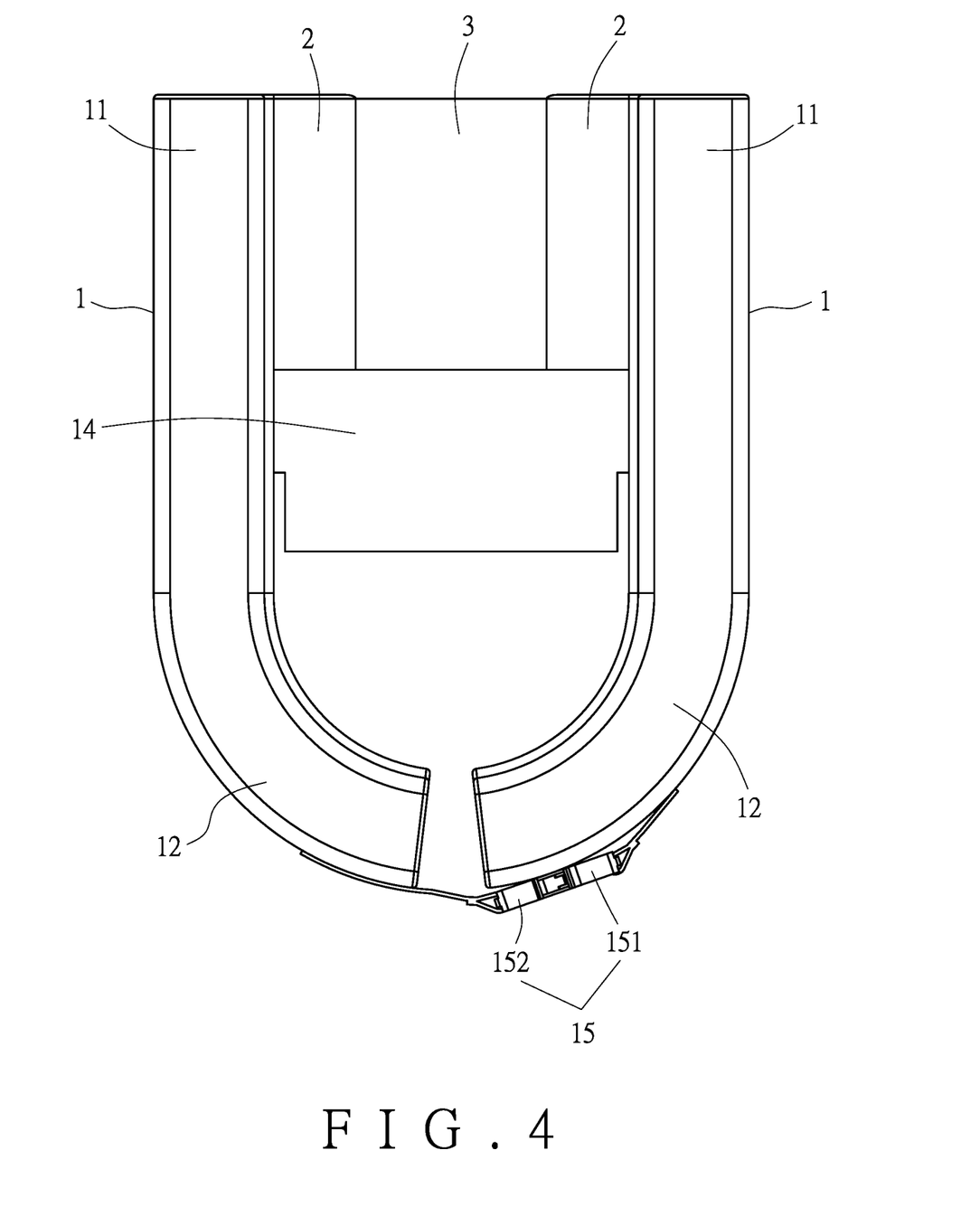
FIG. 4 is a top view in accordance with the first embodiment of the present invention.
Figure 5:
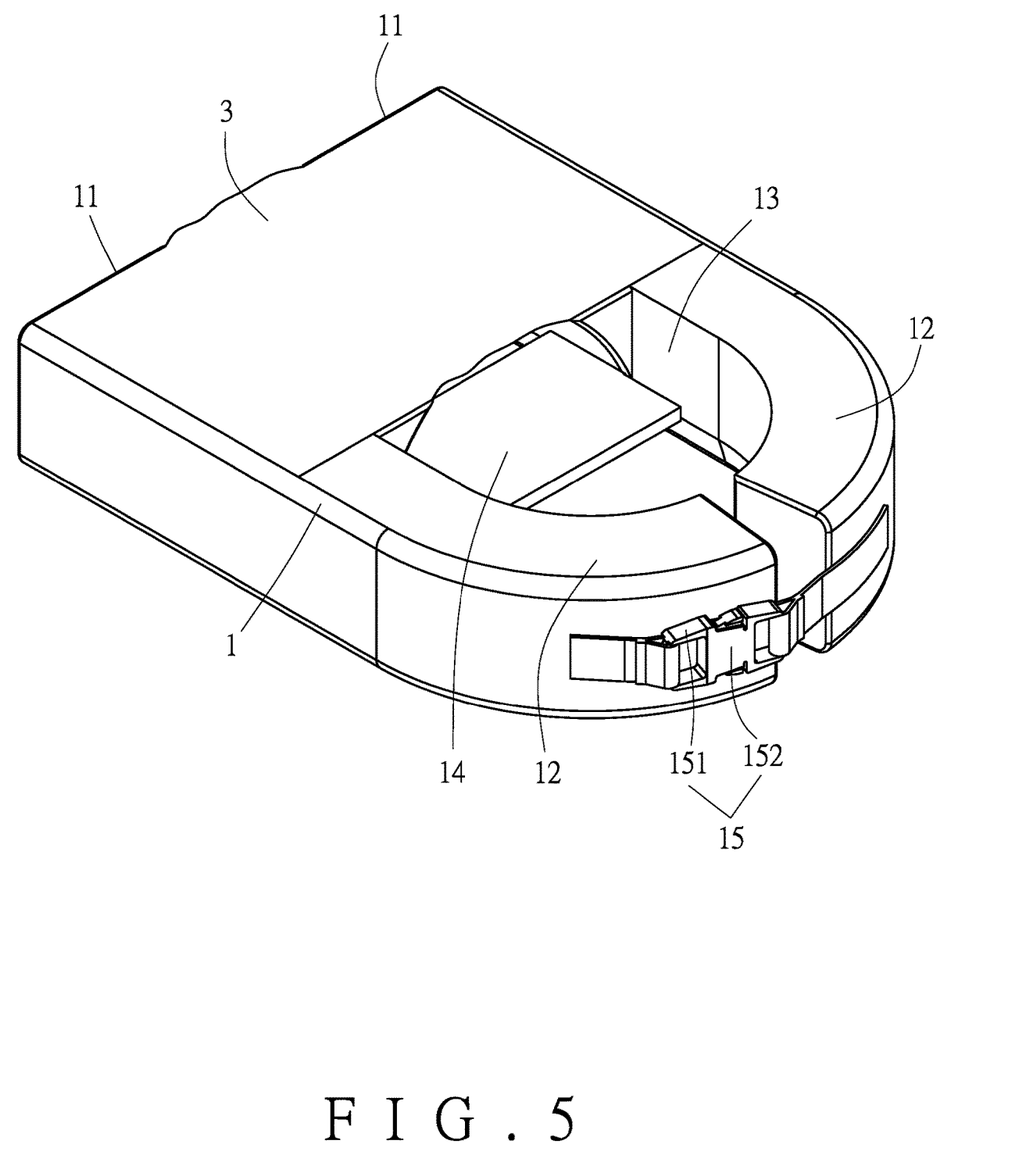
FIG. 5 is a bottom view in accordance with the first embodiment of the present invention.

The two pillow bodies (1) are filled with an elastic filler, such as foam, air, cotton, and silicone. The two pillow bodies (1) each have a first end portion (11) and a second end portion (12). The second end portion (12) is an elongate arc-shaped block. A neck support strap (14), as shown in FIG. 3, is connected between two opposing sides (13) of the two pillow bodies (1). The neck support strap (14) is partially connected to the two opposing sides (13) of the two pillow bodies (1), as shown in FIG. 4, that is to say, the neck support strap (14) is partially separated from the two opposing sides (13) of the two pillow bodies (1). A fastener (15), a fastening strap or a hook-and-loop fastener is connected between the second end portions (12) of the two pillow bodies (1). The fastener (15) includes a male fastening member (151) and a female fastening member (152), so that the male fastening member (151) and the female fastening member (152) are fastened to each other.

The two head support blocks (2) are arc-shaped concave blocks, and are coupled to the first end portions (11) of the two pillow bodies (1). The two head support blocks (2) gradually extend downward from the two opposing sides (13), respectively. The two head support blocks (2) may be integrally formed with the two pillow bodies (1), or may be additionally coupled to the two pillow bodies (1). The two head support blocks (2) are filled with an elastic filler, such as foam, air, cotton, and silicone.

The non-slip layer (3) is connected between the first end portions (11) of the two pillow bodies (1) and between the two head support blocks (2), as shown in FIG. 3. The non-slip layer (3) may be made of a material with a high non-slip coefficient. In addition, the length of the non-slip layer (3) is greater than that of the neck support strap (14), so that the two first end portions (11) can be widened to a relatively large degree, so as to accommodate the heads of different users.

Figure 6:
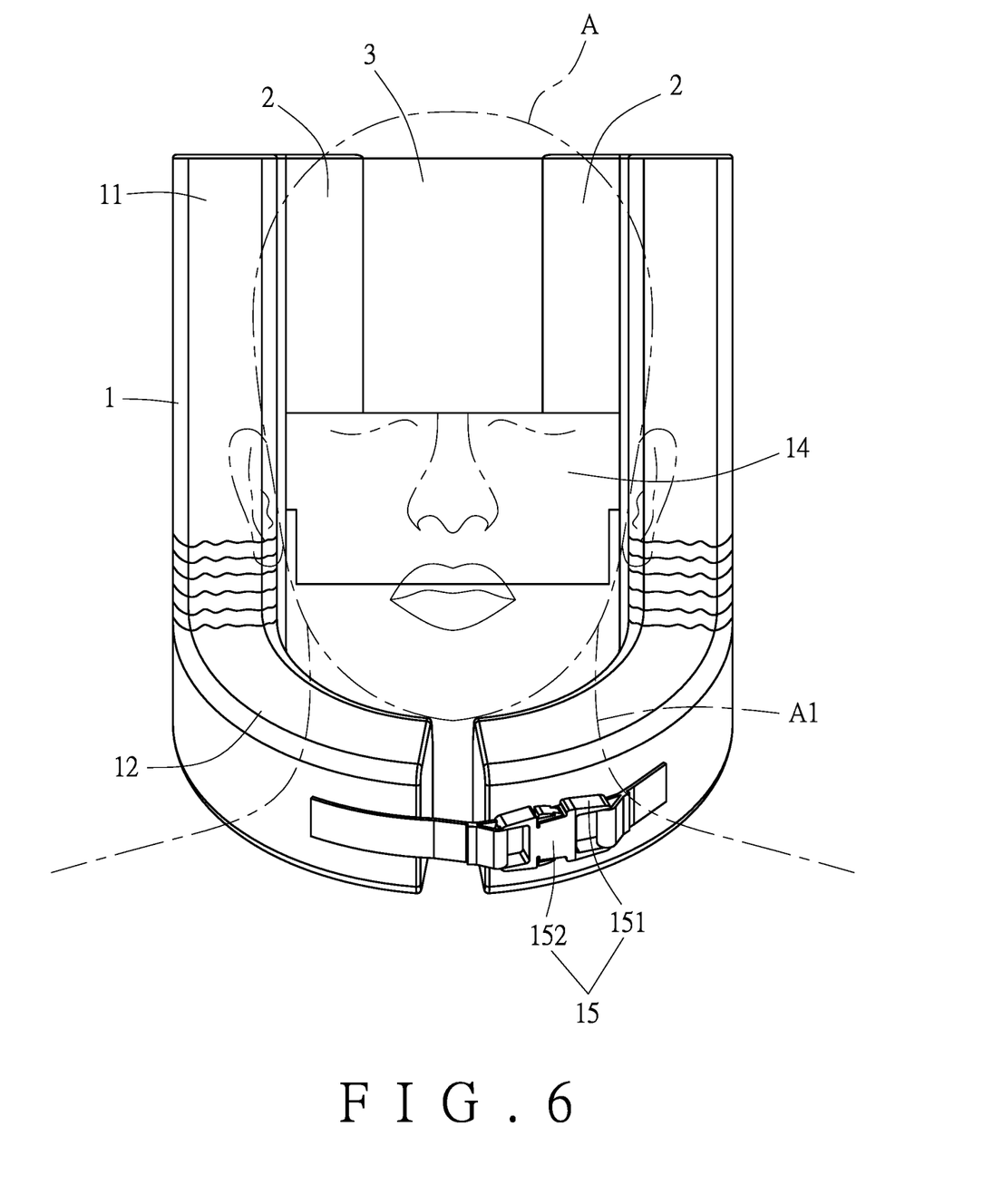
FIG. 6 is a schematic view in accordance with the first embodiment of the present invention when in use.
Figure 7:
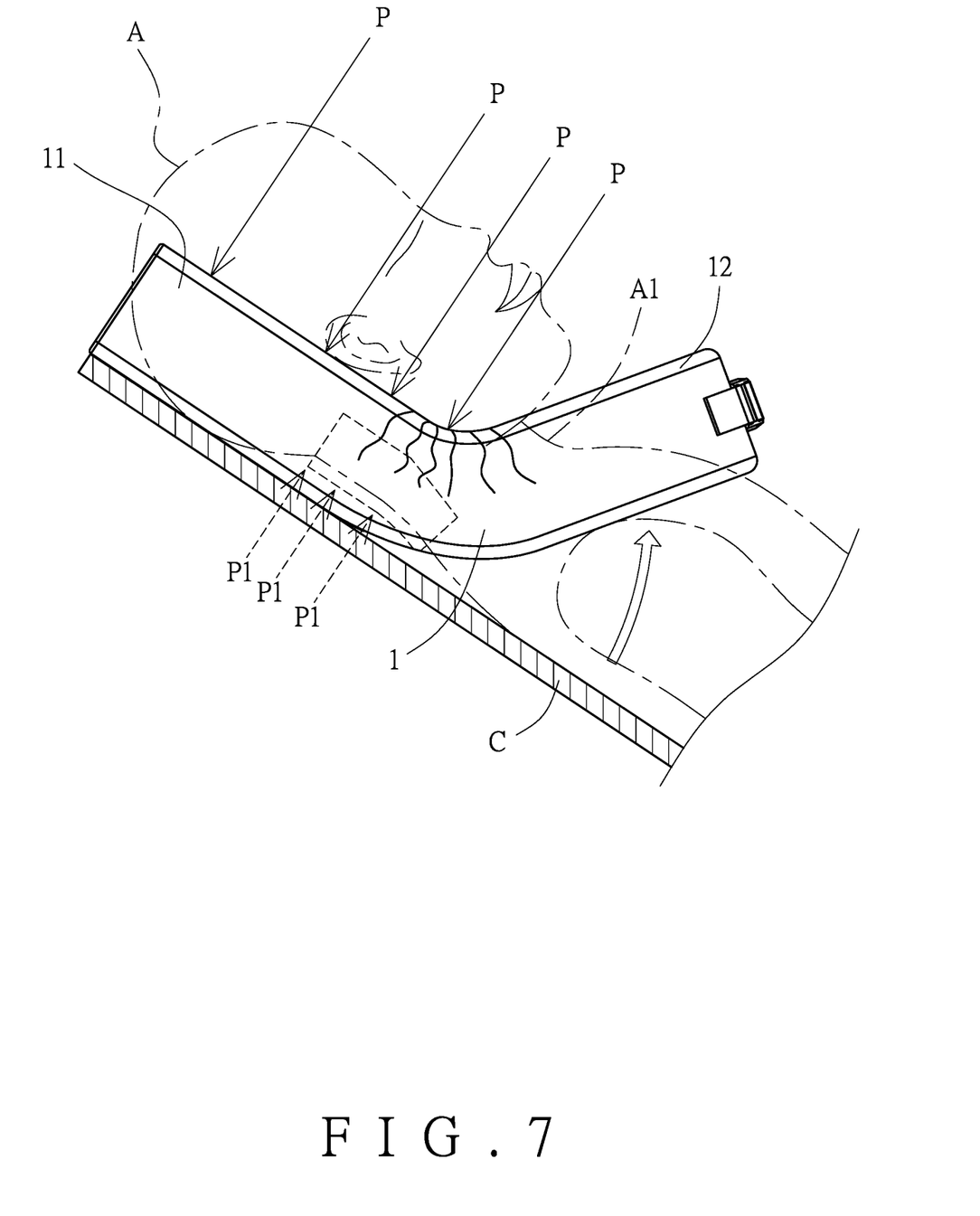
FIG. 7 is a schematic view showing the pressure and force generated by the pillow bodies against the user's head according to the first embodiment of the present invention.

In use, as shown in FIG. 6 and FIG. 7, the two first end portions (11) of the two pillow bodies (1) lean against the back of the user's head (A), and the user's neck (A1) rests on the neck support strap (14), and the two pillow bodies (1) are placed on a seat back (C). Because the two first end portions (11) are subjected to the downward pressure (P) when the head (A) abuts against the two first end portions (11), the two second end portions (12) tilts upward to be curved against the shoulder of the user. The two first end portions (11) of the two pillow bodies (1) and the two head support blocks (2) correspond to the outline of the head (A). The two second end portions (12) are elongate arc-shaped blocks, corresponding to the outline of the user's neck. The male fastening member (151) and the female fastening member (152) are fastened to each other, so that the two second end portions (12) can be tightly fitted to the user's neck. The neck support strap (14) can generate a supporting balanced force (P1) on the user's neck (A1). The seat back (C) bears the weight of the head (A) through the two pillow bodies (1). The user's head (A) and neck (A1) exert the downward pressure (P) on the neck support strap (14), so that the two pillow bodies (1) support the user's neck (A1) and the occipital bone through the reaction force generated by the two pillow bodies (1) due to the elastic deformation. The two first end portions (11) of the two pillow bodies (1) and the two head support blocks (2) can be used to support the center of gravity of the head (A), so that the head (A) and the neck (A1) are kept in a straight line without being offset arbitrarily. The head (A) can be completely surrounded, and the two pillow bodies (1) do not abut against the two sides of the user's cheek. Thus, the head (A) will not skew or lean forward due to muscle relaxation, or the muscles of the neck (A1), the spine and the temporomandibular joint will not be injured by compression, stretching and malocclusion. Therefore, the present invention can achieve the purpose of relaxation and rest.

Figure 8:
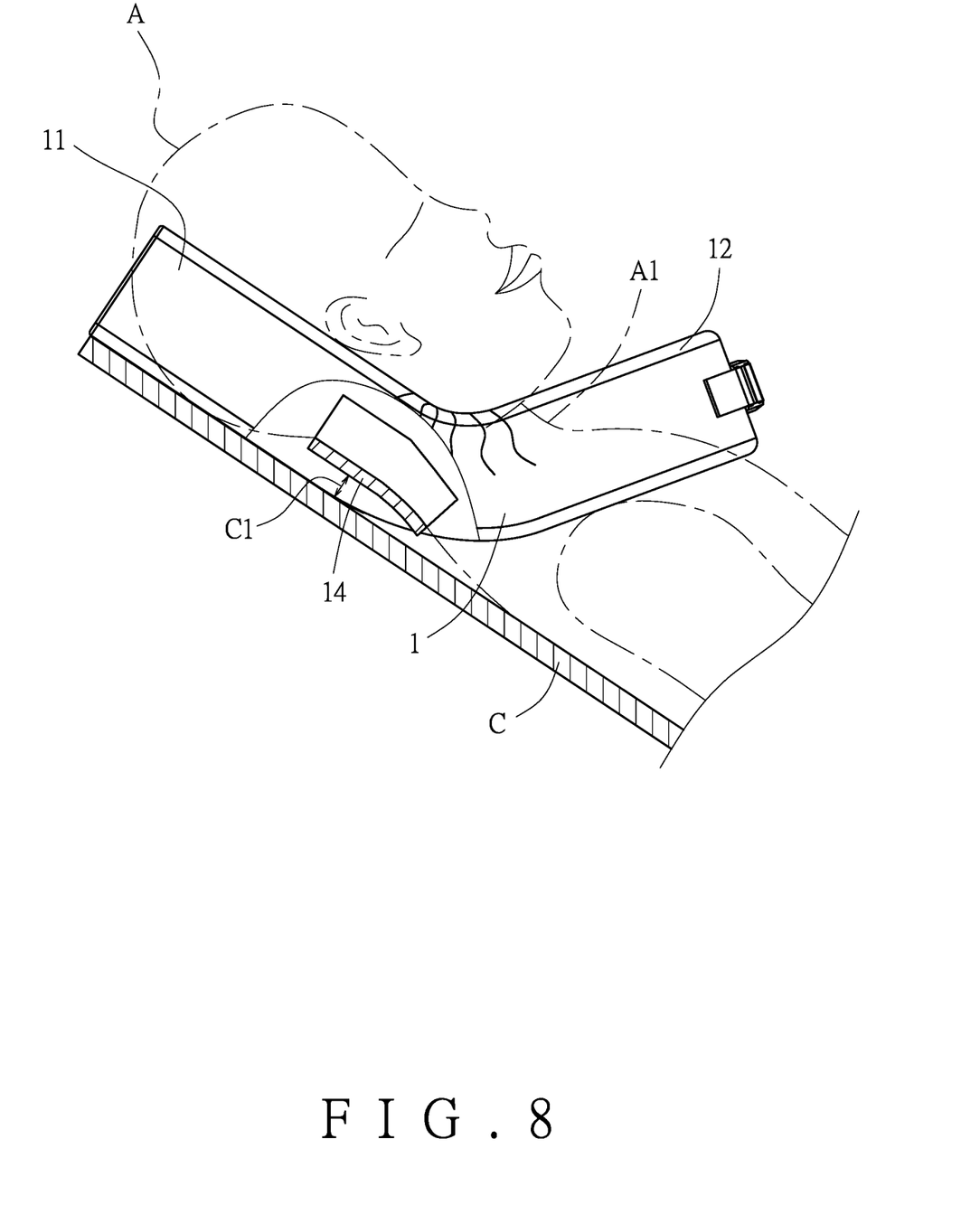
FIG. 8 is a schematic view showing the gap formed between the neck support strap and the seat back according to the first embodiment of the present invention.

As shown in FIG. 8, when the two pillow bodies (1) are placed on the seat back (C), the two second end portions (12) will be curved against the shoulder of the user, and a gap (C1) will be formed between the neck support strap (14) and the seat back (C). Through the gap (C1), air can be circulated and ventilated to dissipate heat, so as to prevent the two pillow bodies (1) from being stuffy when the user's head (A) is rested on the pillow bodies (1). The two first end portions (11), the two head support blocks (2) and the neck support strap (14) can be used to support the user's head (A) and neck (A1). Therefore, a large-area space is formed among the head (A), the neck (A1) and the seat back (C), which is beneficial to ventilate and dissipate heat, so as to achieve a comfortable and cool effect. In particular, the two pillow bodies (1) will not abut against the two sides of the user's cheek to affect the makeup on the user's face, so as to maintain the user's look.

Figure 9:
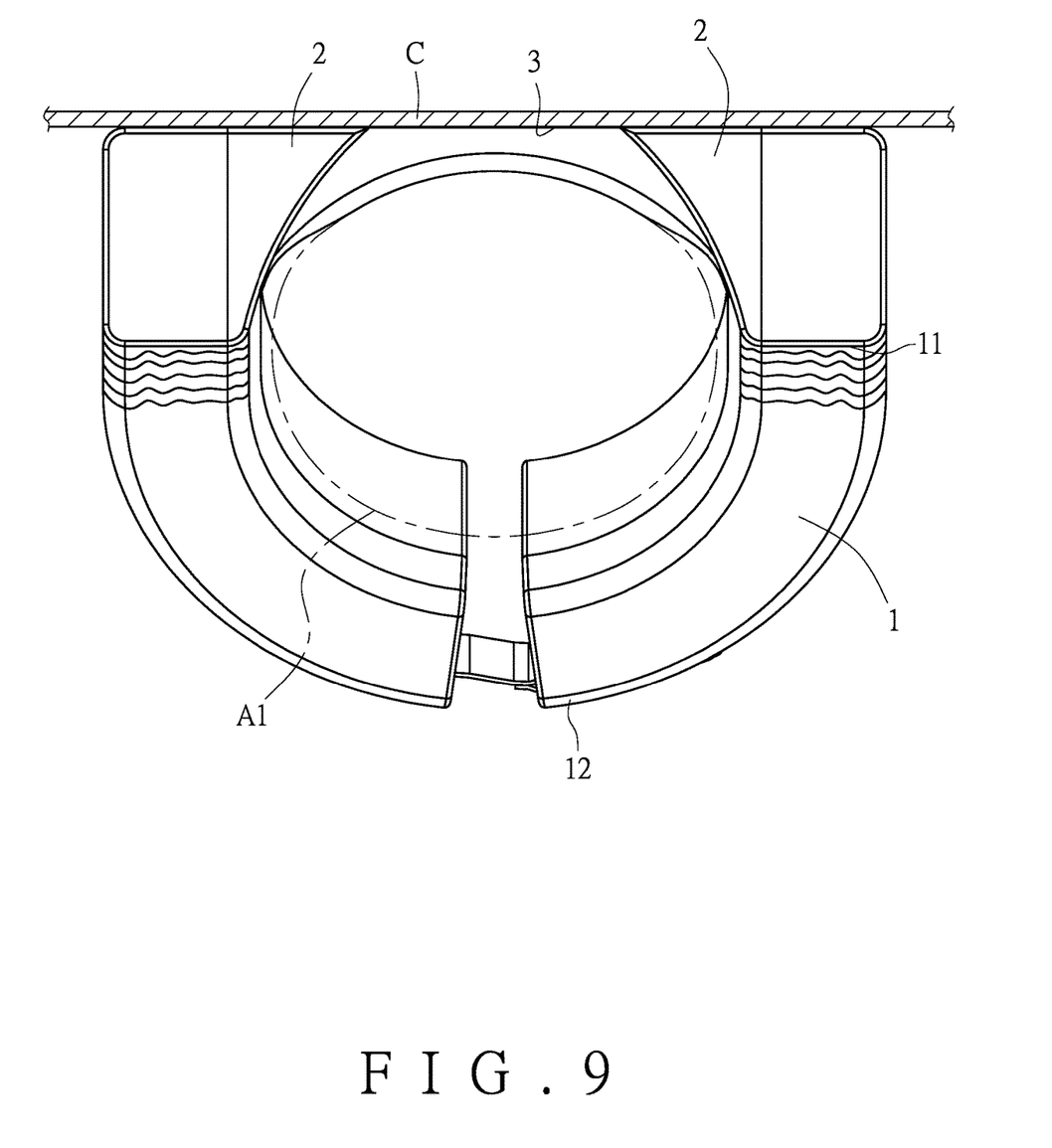
FIG. 9 is a schematic view showing the non-slip layer attached to the seat back according to the first embodiment of the present invention.

As shown in FIG. 9, when the non-slip layer (3) connected between the two first end portions (11) of the two pillow bodies (1) and between the two head support blocks (2) is attached to the seat back (C), the non-slip layer (3) made of a material with a high non-slip coefficient can generate a large frictional force, thereby preventing the two pillow bodies (1) from sliding relative to the seat back (C). It can be more comfortable and stable during sleep, and it is not easy to shake.

In general, there are two causes of temporomandibular arthritis (Data Source: Dr. Ke Zhengyu-temporomandibular arthritis):

1. Derived from muscle: Most of the symptoms comes from abnormal tooth occlusion, a small part comes from that a person grinds his/her teeth in sleep or gnashes his/her teeth in anger or psychological stress, resulting in muscle spasms around the joints. If a person uses an improper pillow for a long time, it may also cause temporomandibular arthritis.

2. Derived from arthrosis: this is relatively rare and comes from the joint degeneration, inflammation, tumor or autoimmune disease. Because the pain innervation of the outer sac and muscle of the temporomandibular joint is the same as that of the ear, it comes from the fifth pair of brain nerves—the trigeminal nerve. Moreover, the temporomandibular joint is close to and in front of the ear. When the temporomandibular joint is painful, the brain will think that the ear innervated by the trigeminal nerve is also painful, so the patient feels ear pain (referred pain). 75% of adults have at least one symptom of a temporomandibular joint on examination epidemiologically, but only 5% of patients need treatments. The male-to-female ratio is 1:4, most in ages of 20-40.

Therefore, the present invention uses the overall structure of the two pillow bodies (1) combined with the neck support strap (14) and the two head support blocks (2) to support the user's head (A) and neck (A1) effectively and stably, without touching the two sides of the user's cheek, so it can effectively prevent the temporomandibular arthritis to ensure the user's health.

When a person rests his/her chin in the hand, the upper cervical vertebrae feels quite strong pressure, and the neck muscles actually contract rather than relax. Therefore, when a person rests his/her chin in the hand, the muscles does not relax, which results in more muscle contraction. When the force to rest one's chin increases, neck muscle contraction increases, and pressure rises. When an improper head rest device is used to rest the chin, the weight of the head is not completely applied to the head rest device. In fact, the reaction force is applied to the chin, which causes the tendency that the head turns to two sides. In order to avoid the tendency that the head turns to the two sides for keeping the head in a neutral position, the muscles of the neck need to resist this reaction force. Therefore, when the weight of the whole body is supported in this posture, the muscles of the neck need to resist with might and main. This will lead to improper use of the body and muscle stiffness. (Data Source: Zhang Guangzu Physical Therapist's Freehand Therapy World) (https://blog.xuite.net/xpung/spine/480531549-

%E6%84%88%E6%89%98%E6%84%88%E7%B4%AF%
E7%9A%84%E7%BE%8E%E4%BA%BA%E6%89%98%
E8%85%AE)

In the present invention, the two first end portions (11) of the two pillow bodies (1) and the two head support blocks (2) correspond to the outline of the head (A), and the neck support strap (14) can generate a supporting balanced force on the user's neck (A1) to counteract the reaction force and support the center of gravity of the head (A), so that the neck (A1) and the head (A) can be kept in a straight line without any offset.

Figure 10:
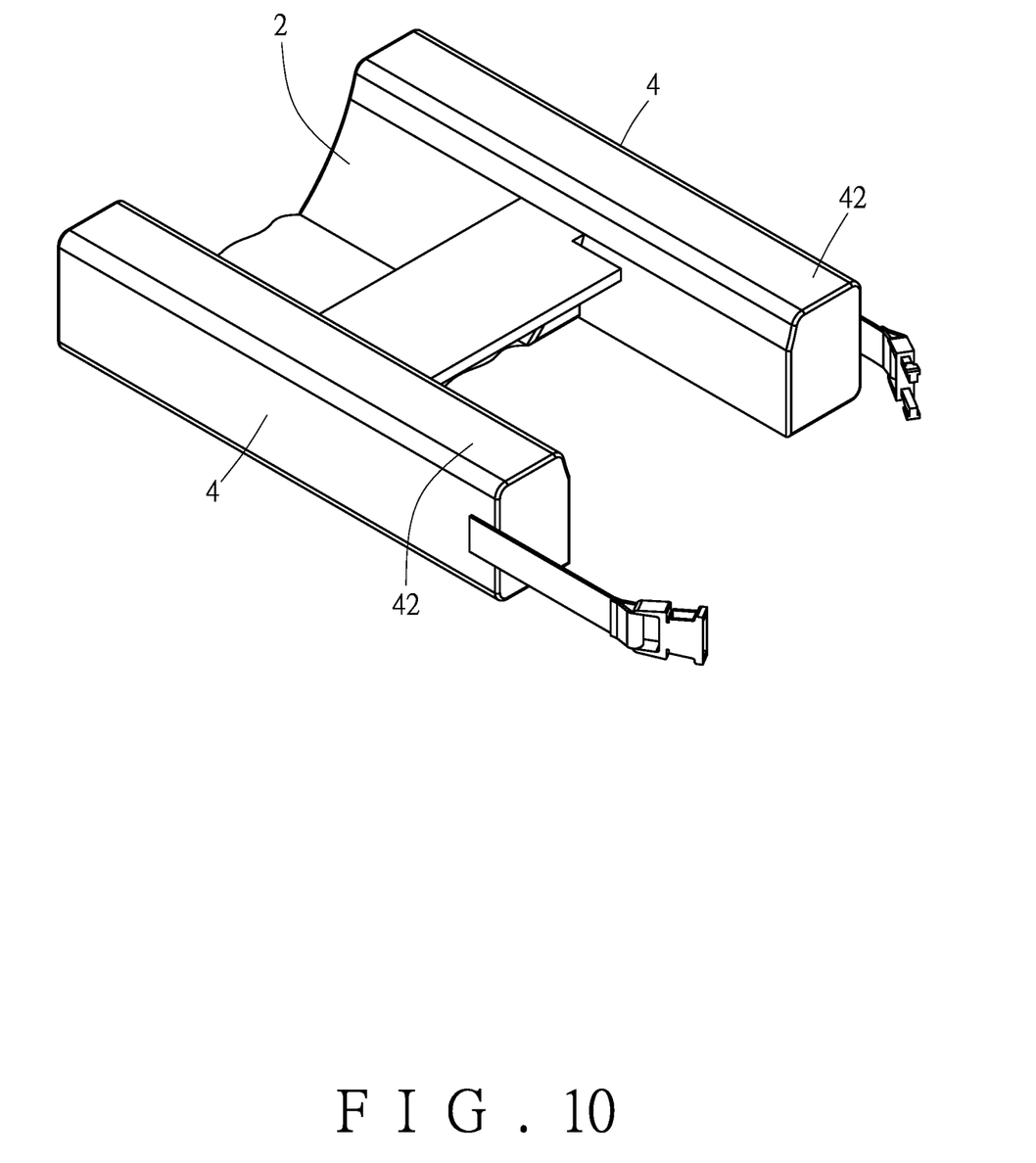
FIG. 10 is a perspective showing the two pillow bodies in the form of an elongate straight block according to a second embodiment of the present invention.

In another embodiment of the present invention, as shown in FIG. 10, the two second end portions (42) of the two pillow bodies (4) are elongate straight blocks, so that the two pillow bodies (4) and the head support blocks (2) can fully surround the user's head, without touching both sides of the cheek, so as to avoid the occurrence of temporomandibular arthritis. Therefore, the present invention can achieve the purpose of relaxation and rest.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A head and neck rest device, comprising:
   two pillow bodies, each of the two pillow bodies having a first end portion and a second end portion, each of the two pillow bodies having opposing inner and outer sidewalls, a neck support strap connected between the inner sidewalls of the two pillow bodies, wherein the neck support strap is located intermediate the first and second end portions of the two pillow bodies;
   two head support blocks coupled to the first end portions of the two pillow bodies, the two head support blocks gradually extending downward from the inner sidewalls of the two pillow bodies, respectively;
   a non-slip layer connected between the first end portions of the two pillow bodies and between the two head support blocks, the non-slip layer being made of a material with a high non-slip coefficient, the non-slip layer having a length greater than that of the neck support strap.

2. The head and neck rest device as claimed in claim 1, wherein the two pillow bodies are filled with an elastic filler selected from one of foam, air, cotton, and silicone.

3. The head and neck rest device as claimed in claim 1, wherein the two pillow bodies are elongate arc-shaped blocks or elongate straight blocks.

4. The head and neck rest device as claimed in claim 1, wherein the two head support blocks are arc-shaped concave blocks.

5. The head and neck rest device as claimed in claim 1, wherein the two head support blocks are integrally formed with the two pillow bodies.

6. The head and neck rest device as claimed in claim 1, wherein the two head support blocks are filled with an elastic filler selected from one of foam, air, cotton, and silicone.

7. The head and neck rest device as claimed in claim 1, wherein the second end portions of the two pillow bodies extend beyond the neck support strap, and a fastener, a fastening strap, or a hook-and-loop fastener is connected between the outer sidewalls of the two pillow bodies adjacent the second end portions of the two pillow bodies.

8. The head and neck rest device as claimed in claim 7, wherein the fastener includes a male fastening member and a female fastening member, the male fastening member and the female fastening member are thereby fastened to each other.

9. The head and neck rest device as claimed in claim 1, wherein the second end portions of the two pillow bodies extend beyond the neck support strap, and are configured to rest against a shoulder portion of a user, each of the two pillow bodies having a fastener element for releasably joining one to the other and are thereby being configured for abutting a user's neck to maintain head and neck alignment.

* * * * *